United States Patent
Barrett et al.

(10) Patent No.: US 9,194,792 B2
(45) Date of Patent: Nov. 24, 2015

(54) BLOOD CHAMBER FOR AN OPTICAL BLOOD MONITORING SYSTEM

(75) Inventors: Louis L. Barrett, West Point, UT (US); Perry N. Law, Kaysville, UT (US)

(73) Assignee: FRESENIUS MEDICAL CARE HOLDINGS, INC., Waltham, MA (US)

(*) Notice: Subject to any disclaimer, the term of this patent is extended or adjusted under 35 U.S.C. 154(b) by 687 days.

(21) Appl. No.: 12/876,572

(22) Filed: Sep. 7, 2010

(65) Prior Publication Data

US 2012/0059234 A1    Mar. 8, 2012

(51) Int. Cl.
| | |
|---|---|
| G01N 21/05 | (2006.01) |
| G01N 21/31 | (2006.01) |
| A61B 5/145 | (2006.01) |
| A61B 5/1455 | (2006.01) |
| A61M 1/36 | (2006.01) |

(52) U.S. Cl.
CPC .............. *G01N 21/05* (2013.01); *A61B 5/1455* (2013.01); *A61B 5/14557* (2013.01); *A61M 1/367* (2013.01); *G01N 21/314* (2013.01); *G01N 21/3151* (2013.01); *A61B 5/14535* (2013.01); *A61B 5/14552* (2013.01); *A61B 2562/185* (2013.01); *A61M 2205/3306* (2013.01); *A61M 2205/3313* (2013.01); *G01N 2021/058* (2013.01); *G01N 2021/3144* (2013.01); *G01N 2021/3148* (2013.01)

(58) Field of Classification Search
None
See application file for complete search history.

(56) References Cited

U.S. PATENT DOCUMENTS

| | | | |
|---|---|---|---|
| D206,714 S | | 1/1967 | Badkar |
| D212,218 S | | 9/1968 | Norton |
| 3,507,951 A | * | 4/1970 | Bailey et al. .................. 264/349 |
| 3,580,683 A | | 5/1971 | Schulkind |
| 3,728,032 A | | 4/1973 | Noll |
| 3,740,156 A | | 6/1973 | Heigl et al. |
| 4,243,883 A | | 1/1981 | Schwarzmann |
| D270,281 S | | 8/1983 | Andersen et al. |
| 4,444,498 A | | 4/1984 | Heinemann |
| 4,784,768 A | | 11/1988 | Mathieu |
| 4,936,993 A | | 6/1990 | Nomura |
| 5,073,171 A | * | 12/1991 | Eaton ............................ 604/266 |
| 5,171,456 A | | 12/1992 | Hwang et al. |
| D335,096 S | | 4/1993 | Marsch |
| 5,222,948 A | | 6/1993 | Austin et al. |
| 5,231,464 A | | 7/1993 | Ichimura et al. |
| 5,247,434 A | | 9/1993 | Peterson et al. |

(Continued)

FOREIGN PATENT DOCUMENTS

| | | |
|---|---|---|
| CN | 101015455 A | 8/2007 |
| EP | 0 274 178 A1 | 7/1988 |

(Continued)

OTHER PUBLICATIONS

Blood Chamber 2001—Admitted Prior Art.

(Continued)

*Primary Examiner* — Gordon J Stock, Jr.
(74) *Attorney, Agent, or Firm* — Leydig, Voit & Mayer, Ltd.

(57) ABSTRACT

An extracorporeal blood chamber for an optical blood monitoring system includes an opaque chamber body in order to prevent inaccuracies when measuring oxygen saturation levels due to light ducting, which can occur at low oxygen saturation levels and low hematocrit levels. In one embodiment, the blood chamber need not include a moat as is present in conventional blood chambers.

17 Claims, 9 Drawing Sheets

(56) References Cited

U.S. PATENT DOCUMENTS

| | | | |
|---|---|---|---|
| 5,312,535 A | 5/1994 | Waska et al. | |
| 2,357,238 A | 8/1994 | Trimble | |
| 5,351,686 A | 10/1994 | Steuer et al. | |
| 5,366,630 A | 11/1994 | Chevallet | |
| 5,372,136 A | 12/1994 | Steuer et al. | |
| 5,456,253 A | 10/1995 | Steuer et al. | |
| 5,458,566 A | 10/1995 | Herrig et al. | |
| 5,476,764 A | 12/1995 | Bitensky | |
| 5,531,686 A | 7/1996 | Lundquist et al. | |
| 5,670,050 A | 9/1997 | Brose et al. | |
| 5,674,390 A | 10/1997 | Matthews et al. | |
| 5,676,644 A | 10/1997 | Toavs et al. | |
| 5,729,333 A | 3/1998 | Osten et al. | |
| 5,730,712 A | 3/1998 | Falkvall et al. | |
| 5,762,805 A | 6/1998 | Truitt et al. | |
| 5,769,815 A | 6/1998 | Utterberg | |
| 5,779,529 A * | 7/1998 | Bizer | 451/550 |
| 5,792,052 A | 8/1998 | Isaacson et al. | |
| D409,750 S | 5/1999 | Hacker | |
| 6,018,673 A * | 1/2000 | Chin et al. | 600/322 |
| 6,069,687 A | 5/2000 | Briggs | |
| 6,090,061 A | 7/2000 | Steuer et al. | |
| 6,284,131 B1 | 9/2001 | Hogard et al. | |
| 6,284,142 B1 | 9/2001 | Muller | |
| 6,510,330 B1 | 1/2003 | Enejder | |
| 6,746,415 B1 | 6/2004 | Steuer et al. | |
| 6,784,820 B1 | 8/2004 | Casalegno et al. | |
| 7,018,353 B2 | 3/2006 | Hunley et al. | |
| D518,573 S | 4/2006 | French | |
| 7,241,825 B2 * | 7/2007 | Koga et al. | 524/311 |
| 7,247,143 B2 * | 7/2007 | Law et al. | 600/499 |
| 7,671,974 B2 | 3/2010 | O'Mahony et al. | |
| D623,302 S | 9/2010 | Barrett et al. | |
| D625,824 S | 10/2010 | Brackett et al. | |
| D630,536 S | 1/2011 | Pettit | |
| D654,999 S * | 2/2012 | Barrett et al. | D24/129 |
| 8,133,194 B2 | 3/2012 | Szamosfalvi et al. | |
| 8,287,739 B2 | 10/2012 | Barrett et al. | |
| 8,315,682 B2 | 11/2012 | Such et al. | |
| 8,328,748 B2 * | 12/2012 | Law et al. | 604/4.01 |
| 8,333,724 B2 * | 12/2012 | Barrett et al. | 604/5.01 |
| D684,695 S | 6/2013 | Green et al. | |
| D684,697 S | 6/2013 | Green et al. | |
| 8,517,968 B2 * | 8/2013 | Barrett et al. | 604/6.09 |
| D698,440 S | 1/2014 | Lombardi et al. | |
| 2001/0016699 A1 | 8/2001 | Burbank et al. | |
| 2001/0021817 A1 | 9/2001 | Brugger et al. | |
| 2001/0037079 A1 | 11/2001 | Burbank et al. | |
| 2001/0041892 A1 | 11/2001 | Burbank et al. | |
| 2002/0103453 A1 | 8/2002 | Burbank et al. | |
| 2002/0147423 A1 | 10/2002 | Burbank et al. | |
| 2003/0009123 A1 | 1/2003 | Brugger et al. | |
| 2003/0045784 A1 | 3/2003 | Palatnik et al. | |
| 2003/0070969 A1 | 4/2003 | Muller et al. | |
| 2003/0097087 A1 | 5/2003 | Gura | |
| 2003/0143116 A1* | 7/2003 | Zheng et al. | 422/68.1 |
| 2003/0196949 A1 | 10/2003 | Sunohara et al. | |
| 2003/0210390 A1 | 11/2003 | O'Mahony et al. | |
| 2003/0212316 A1 | 11/2003 | Leiden | |
| 2004/0087845 A1 | 5/2004 | Katarow et al. | |
| 2005/0094127 A1 | 5/2005 | O'Mahony et al. | |
| 2006/0036185 A1 | 2/2006 | Lewicke et al. | |
| 2006/0144776 A1 | 7/2006 | Mishkin et al. | |
| 2006/0226079 A1 | 10/2006 | Mori et al. | |
| 2006/0290625 A1 | 12/2006 | Sugimoto | |
| 2007/0015963 A1* | 1/2007 | Fengler et al. | 600/109 |
| 2007/0100219 A1 | 5/2007 | Sweutzer et al. | |
| 2007/0149871 A1 | 6/2007 | Sarussi et al. | |
| 2007/0179433 A1 | 8/2007 | Jonsson et al. | |
| 2008/0081970 A1 | 4/2008 | Boyce et al. | |
| 2008/0129047 A1 | 6/2008 | Blivet et al. | |
| 2008/0300570 A1 | 12/2008 | Fowles et al. | |
| 2009/0054751 A1 | 2/2009 | Babashan et al. | |
| 2010/0004518 A1* | 1/2010 | Vo et al. | 600/310 |
| 2010/0110416 A1 | 5/2010 | Barrett et al. | |
| 2010/0113891 A1 | 5/2010 | Barrett et al. | |
| 2010/0168531 A1 | 7/2010 | Shaltis et al. | |
| 2011/0004082 A1 | 1/2011 | Poeze et al. | |
| 2011/0022077 A1 | 1/2011 | Green et al. | |
| 2011/0160679 A1 | 6/2011 | Okiyama et al. | |
| 2012/0120384 A1 | 5/2012 | Barrett et al. | |
| 2012/0154789 A1 | 6/2012 | Barrett et al. | |

FOREIGN PATENT DOCUMENTS

| | | | |
|---|---|---|---|
| EP | 467805 A1 | | 1/1992 |
| EP | 0 990 444 A2 | | 4/2000 |
| GB | 1 583 023 | | 1/1981 |
| JP | 56031085 A | * | 3/1981 |
| JP | 09-229847 | | 9/1997 |
| JP | 2006199845 A | * | 8/2006 |
| JP | 2009-216711 | | 9/2009 |
| WO | WO 93/06456 A1 | | 4/1993 |
| WO | WO 93/06774 A1 | | 4/1993 |
| WO | WO 9427495 A1 | | 12/1994 |
| WO | WO 98/37801 A1 | | 9/1998 |
| WO | WO 00/33053 | | 6/2000 |
| WO | WO 0187151 A2 | | 11/2001 |
| WO | WO 01/93944 A1 | | 12/2001 |
| WO | WO 02/078783 A2 | | 10/2002 |

OTHER PUBLICATIONS

CL Photo 2000—Admitted Prior Art.

Blood Chamber Instruction Sheet 2001—Admitted Prior Art.

Office action for co-pending .Canadian Patent Application No. 2,742,619, dated Aug. 5, 2013.

Original claims as filed for co pending Canadian Patent Application No. 2,742,619, including a Voluntary Amendment dated Sep. 6, 2011.

Office action for co-pending Canadian Patent Application No. 2,742,794, including original claims as filed.

Official action for co-pending European Patent Application No. 11 755 533.4 dated Apr. 16, 2013.

Official action for co-pending European Patent Application No. 11 754 974.1 dated Apr. 16, 2013.

International Search Report and Written Opinion for related International No. PCT/US2012/026637 dated Jun. 6, 2012).

Sacker-Berstein, Jonathan D., M.D., et al., "How SHould Diuretic-Refractory Colume-OVerloaded Heart Failure Patients Be Managed?", *The Journal of Invasive Cardiology*, vol. 15., No. 10 (Oct. 2003), pp. 585-590, retrieved from http://www.medscape.com/viewarticle/463509_print on Mar. 11, 2013, pp. 1-11.

Jaski, Brian E., M.D., "Peripherally Inserted Veno-Venous Ultrafiltration for Rapid Treatment of Volume Overloaded Patients", *Journal of Cardiac Failure*, vol. 9, No. 3 (Jun. 2003) pp. 227-231.

Steuer, et al., "Optical Measurement of Hematocrit and Other Biological Constituents in Renal Therapy", *Advances in Renal Replacement Therapy*, vol. 6, No. 3 (Jul. 1999), pp. 217-224).

Gardner, "Exponential Smoothing: The State of Art", *Journal of Forecasting*, vol. 4, 1985, (pp. 1-28).

Baum, "An Introduction to Modern Econometrics Using Strata", *StaraCorp., LP,* 2006, Chapter 9, (pp. 2165-2245).

International Search Report and Written Opinion for International No. PCT/US2009/057964, dated Jun. 18, 2010.

Logman, Dirren H., MHGM, et al., "Altitude Correction fro Hemoglobin", *European Journal of Clinical Nutrition*, (Believed to be no longer in publication).

Peer Review, "Effects of CPD and K2EDTA Preservatives on Blood Sample Hematocrit", Asaio Abstract Submission Information, *45th Annual Conference,* San Diego, Jun. 3-5, 1999.

Zhang, S., Ph.D., et al., Hematocrit Measurement Error Due to Time Dependence of Hematocrit fro EDTA-Preserved Blood Samples, *ANA 36 Annual Meeting & Scientific Exposition,* http//www.call4abstracts.com/ams/main/finalpreview, site visited Jun. 25, 2003.

Crit-Line Hematrocrt Accuracy Hema Metrics, vol. 1, Tech Note No. 11 (Rev D), pp. 1-4, Feb. 24, 2003.

*ScienceStockroom Flow Through Cuvette,* p. 8/14.

International Search Report of International Application No. PCT/US2011/061273 (Mar. 13, 2012).

(56) References Cited

OTHER PUBLICATIONS

Barrett, Lee, "Effects of CPD and $K_3$ *EDTA Preservatives on Blood Sample Hematocrit*", *Abstract Submission, ASAIO, 45th Annual Conference,* San Diego (Jun. 1999).

Cohen, Jennifer H., et al., "Hemoglobin Correction Factors for Estimating the Prevalence of Iron Deficiency Anemia in Pregnant Women Residing at High Altitudes in Bolivia", retrieved from http://www.scielo.php?script=sci_arttext&pid=S1020-49891999001100004 on Jun. 19, 2009 (12 pages).

Official Action from co-pending Canadian Patent Application No. 2,742,619, dated Nov. 6, 2014, (5 pages).

Chinese Office Action for Chinese Patent Application No. 201180055375.2, dated Mar. 16, 2015 (43 pages total).

Japanese Office action for Japanese Patent Application No. 58245/2013, dated Dec. 24, 2014, (5 pages).

Chinese Office for Chinese Patent Application No. 201180042991.4, dated Jan. 19, 2015, (9 pages).

\* cited by examiner

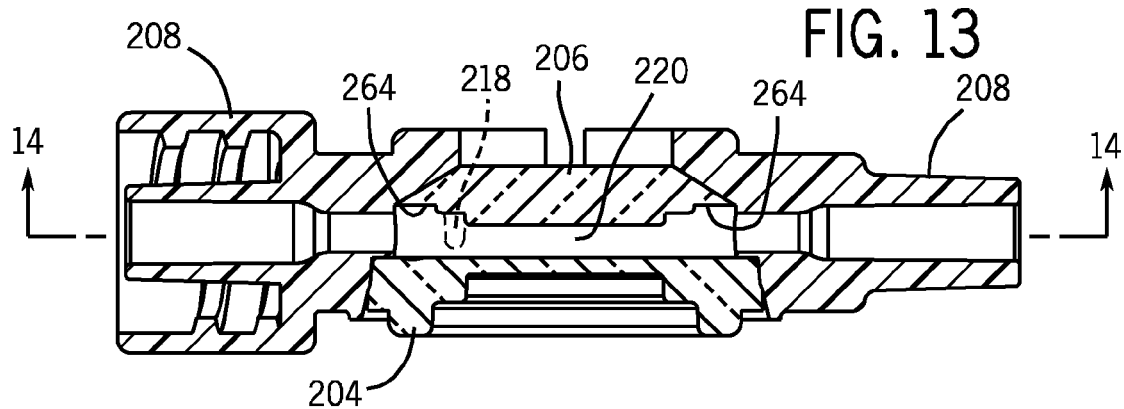
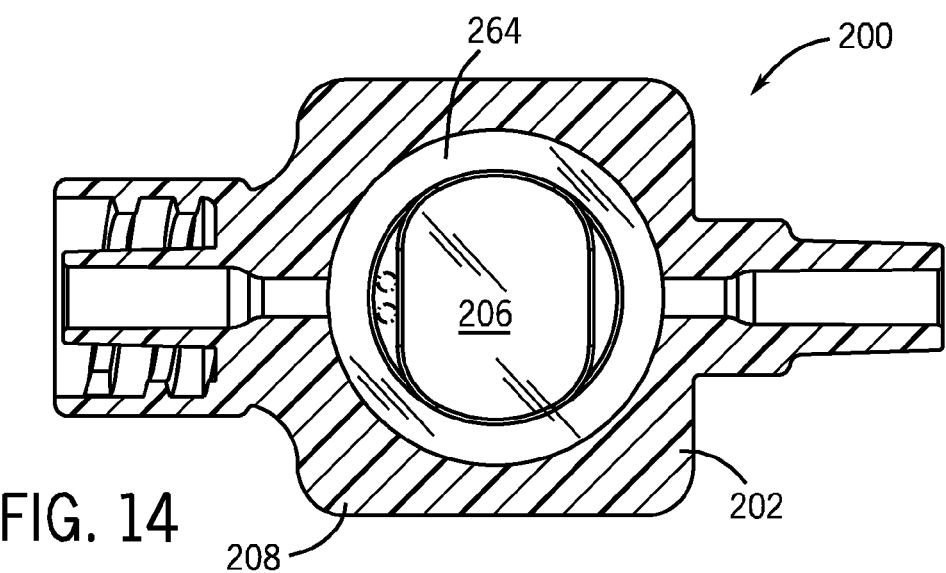

BLOOD CHAMBER FOR AN OPTICAL BLOOD MONITORING SYSTEM

FIELD OF THE INVENTION

The invention relates to optical blood monitoring systems, and in particular, single-use blood chambers for the real-time measurement of hematocrit, oxygen saturation levels and/or other blood constituents. The blood chambers are useful when monitoring extracorporeal patient blood flow. The invention is particularly directed to improving the reliability of low level oxygen saturation measurements.

BACKGROUND

The type of blood chambers to which the invention pertains have been widely used to monitor a patient's hematocrit and oxygen saturation levels during conventional hemodialysis treatments. Patients with kidney failure or partial kidney failure typically undergo hemodialysis treatment in order to remove toxins and excess fluids from their blood. To do this, blood is taken from a patient through an intake needle or catheter which draws blood from an artery located in a specifically accepted access location (for example, a shunt surgically placed in an arm, thigh, subclavian, etc.). The needle or catheter is connected to extracorporeal tubing that is fed to a peristaltic pump and then to a dialyzer that cleans the blood and removes excess water. The cleaned blood is then returned to the patient through additional extracorporeal tubing and another needle or catheter. Sometimes, a heparin drip is located in the hemodialysis loop to prevent the blood from coagulating. By way of background, as the drawn blood passes through the dialyzer, it travels in straw-like tubes within the dialyzer which serve as semi-permeable passageways for the unclean blood. Fresh dialysate solution enters the dialyzer at its downstream end. The dialysate surrounds the straw-like tubes and flows through the dialyzer in the opposite direction of the blood flowing through the tubes. Fresh dialysate collects toxins passing through the straw-like tubes by diffusion and excess fluids in the blood by ultra filtration. Dialysate containing the removed toxins and excess fluids is disposed of as waste.

It is known in the art to use an optical blood monitoring system during hemodialysis, such as the CRIT-LINE® monitoring system sold by the assignee of this application. The current CRIT-LINE® blood monitoring system uses optical techniques to non-invasively measure in real-time the hematocrit and the oxygen saturation level of blood flowing through a hemodialysis system or other systems involving extracorporeal blood flow. When the CRIT-LINE® system is used with conventional hemodialysis systems, a sterile, single-use blood chamber is usually attached in-line to the extracorporeal tubing on the arterial side of the dialyzer. The blood chamber provides a viewing point for optical sensors during the hemodialysis procedure. Multiple wavelengths of light are directed through the blood chamber and the patient's blood flowing through the chamber, and a photodetector detects the resulting intensity of each wavelength. The preferred wavelengths to measure hematocrit are about 810 nm (e.g. 829 nm), which is substantially isobestic for red blood cells, and about 1300 nm, which is substantially isobestic for water. A ratiometric technique implemented in the CRIT-LINE® controller, substantially as disclosed in U.S. Pat. No. 5,372,136 entitled "System and Method for Non-Invasive Hematocrit Monitoring", which issued on Dec. 13, 1999 and assigned to the assignee of the present application, uses this information to calculate the patient's hematocrit value in real-time. The hematocrit value, as is widely used in the art, is the percentage determined by dividing the volume of the red blood cells in a given whole blood sample by the overall volume of the blood sample.

In a clinical setting, the actual percentage change in blood volume occurring during hemodialysis can be determined, in real-time, from the change in the measured hematocrit. Thus, an optical blood monitor, such as the CRIT-LINE® monitor, is able to non-invasively monitor not only the patient's hematocrit level but also the change in the patient's blood volume in real-time during a hemodialysis treatment session. The ability to monitor real-time change in blood volume facilitates safe, effective hemodialysis.

The mathematical ratiometric model for determining the hematocrit (HCT) value can be represented by the following equation:

$$HCT = f\left[\frac{\ln\left(\frac{i_{810}}{I_{0-810}}\right)}{\ln\left(\frac{i_{1300}}{I_{0-1300}}\right)}\right] \qquad \text{Eq. (1)}$$

where $i_{810}$ is the infrared intensity detected by the photoreceiver at 810 nm, $i_{1300}$ is the infrared intensity detected at 1300 nm and $I_{0-810}$ and $I_{0-1300}$ are constants representing the infrared intensity incident on the blood accounting for losses through the blood chamber. The function $f[\ ]$ is a mathematical function which has been determined based on experimental data to yield the hematocrit value. Preferably, the function $f[\ ]$ in the above Equation (1) is a relatively simply polynomial, e.g. a second order polynomial. The above Equation (1) holds true only if the distance traveled by the infrared radiation from the LED emitter to the photodetectors at both wavelengths is a constant distance.

The mathematical ratiometric model for determining oxygen saturation level (SAT) can be represented by the following equation:

$$SAT = g\left[\frac{\ln\left(\frac{i_{660}}{I_{0-660}}\right)}{\ln\left(\frac{i_{810}}{I_{0-810}}\right)}\right] \qquad \text{Eq. (2)}$$

where $i_{660}$ is the light intensity of the photoreceiver at 660 nm, $i_{810}$ is the detected intensity at 810 nm and $I_{0660}$ and $I_{0829}$ are constants representing the intensity incident on the blood accounting for losses through the blood chamber. The function $g[\ ]$ is a mathematical function determined based on experimental data to yield the oxygen saturation level, again preferably a second order polynomial. Also, like Equation (1) for the hematocrit calculation, Equation (2) for the oxygen saturation level calculation holds true only if the distance traveled by the light and infrared radiation from the respective LED emitter to the respective detector at both the 660 nm and 810 nm wavelengths is a constant distance. Similar as in the case with the calculation for hematocrit, errors in the oxygen saturation value can occur if there are errors in the measured intensity at the 660 nm or 810 nm wavelength. And also, while such errors are not common, the most prolific source of such errors is ducting of light through the blood chamber.

As described in more detail below under the heading Detailed Description of the Drawings, the blood chamber used in the current system comprises a molded body made of clear, medical-grade polycarbonate. The chamber body along with the tube set and dialyzer are replaced for each patient and the blood chamber is intended for a single use. The blood chamber provides an internal blood flow cavity, a flat viewing region and two viewing lenses: one being integrally molded with the body of the polycarbonate blood chamber and the other being welded into place. The LED emitters and photodetectors for the optical blood monitor are clipped into place on the blood chamber over the lenses.

The clear polycarbonate blood chamber tends to duct visible light and infra-red light from the LED emitters so that some of the light intensity sensed by the detectors does not pass through the same distance as along the direct path from the LED emitter to the detector through the blood flow in the viewing area. If this stray visible light or stray infra-red light is not attenuated, the system can generate an error that is not easily modeled or extracted during calibration. The prior art blood chamber is molded with a moat around the flat viewing region in the blood flow cavity between the viewing lenses. The moat holds a relatively thick layer of blood, and helps to attenuate ambient light as well as light piping inaccuracies. The blood-filled moat attenuates visible and infrared light that has ducted through the chamber and refracted on a path towards the respective photodetector.

It has been discovered that, even with a moat, errors due to light ducting can occur when making low level oxygen saturation measurements if the patient has a very low hematocrit level (e.g. HCT<about 15).

The full dynamic range for the oxygen saturation signal through blood at the 660 nm wavelength is approximately 500:1. For normal hematocrit levels, the moat in the blood chamber is full of red blood cells and sufficiently isolates the photodetector from ducted light at the 660 nm wavelength so that the measurement of oxygen saturation levels is accurate over the entire dynamic range of expected oxygen saturation levels. However, when the patient's hematocrit drops below about 15 there are fewer red blood cells in the moat and its signal isolation capabilities are compromised. Under these circumstances, light piping can cause inaccuracies in the detection of oxygen saturation levels. As mentioned, the calculation of the oxygen saturation level is based on a ratiometric model of detected intensities at 660 nm (red) and 810 nm (infrared) after the radiation passes through the blood chamber lenses and the blood flowing through the blood chamber. It has been experienced that the expected dynamic range of the signals at 810 nm is about 20:1 whereas the expected dynamic range of the signals at 660 nm is about 500:1. Due in part to the large expected dynamic range of the signals at 660 nm, error introduced by light piping (at low HCT levels) competes with the resolution of the oxygen saturation signal at low levels.

In recent years, the CRIT-LINE® optical blood monitor has been used in more applications where the access point for the extracorporeal blood draw is through a catheter containing the patient's venous blood. Nearly all patients with serious illness or condition have a low hematocrit level. Low hematocrit levels facilitate more errant light piping in the current blood chamber as the red cell content in the moat depletes. The measurement accuracy of oxygen saturation levels is thereby compromised. Such applications where venous measurements are made can include major surgery and in intensive care units, Current studies indicate a strong correlation between venous oxygen saturation level and cardiac output. A typical oxygen saturation level for a healthy individual might be 95% for arterial blood and about 65% for venous blood. A venous oxygen saturation level of 50% or below would raise reason for concern for the patient's condition. The need to accurately measure low oxygen saturation levels in venous blood in particular is becoming more prevalent in these types of applications in addition to the conventional hemodialysis applications. Other applications in which low oxygen saturation levels are somewhat more likely are also becoming more prevalent.

SUMMARY OF THE INVENTION

A primary objective of the invention is to facilitate the accurate measurement of oxygen saturation levels over the full expected dynamic range of the detected signals used to calculate oxygen saturation levels via a ratiometric model, and to do so at both high and low hematocrit levels.

The invention pertains to a blood chamber having a chamber body that is made at least partially of a material that is opaque to red light having the same wavelength as one of the wavelengths used in a ratiometric model to calculate oxygen saturation levels of blood flowing through the blood chamber. For this purpose, a blue-tinted chamber body may be used to attenuate the red light ducting through the chamber body and isolate the lenses from the ducted light, thereby avoiding inaccuracies in the measurement of oxygen saturation levels that can accompany the measurement of low levels of oxygen saturation when the patient has a low hematocrit value.

Some signal processing techniques do not adequately account for the effects of ambient light, and in these applications the moat is most likely critical to attenuate infrared light at about 810 nm and 1300 nm even if the chamber body is blue-tinted to attenuate visible 660 nm red light. A secondary objective of the invention, however, is to enable the removal of the moat in the design of the blood chamber and yet maintain reliable oxygen saturation measurement accuracy for systems in which the effects of ambient light are not an issue.

Other objects and advantages of the invention will be apparent to those skilled in the art upon reviewing the following drawings and description thereof.

BRIEF DESCRIPTION OF THE DRAWINGS

FIG. 13 is a longitudinal sectional view of the second embodiment.

FIG. 14 is a sectional view taken along line 14-14 in FIG. 13.

DETAILED DESCRIPTION

Prior Art

Figure 1:
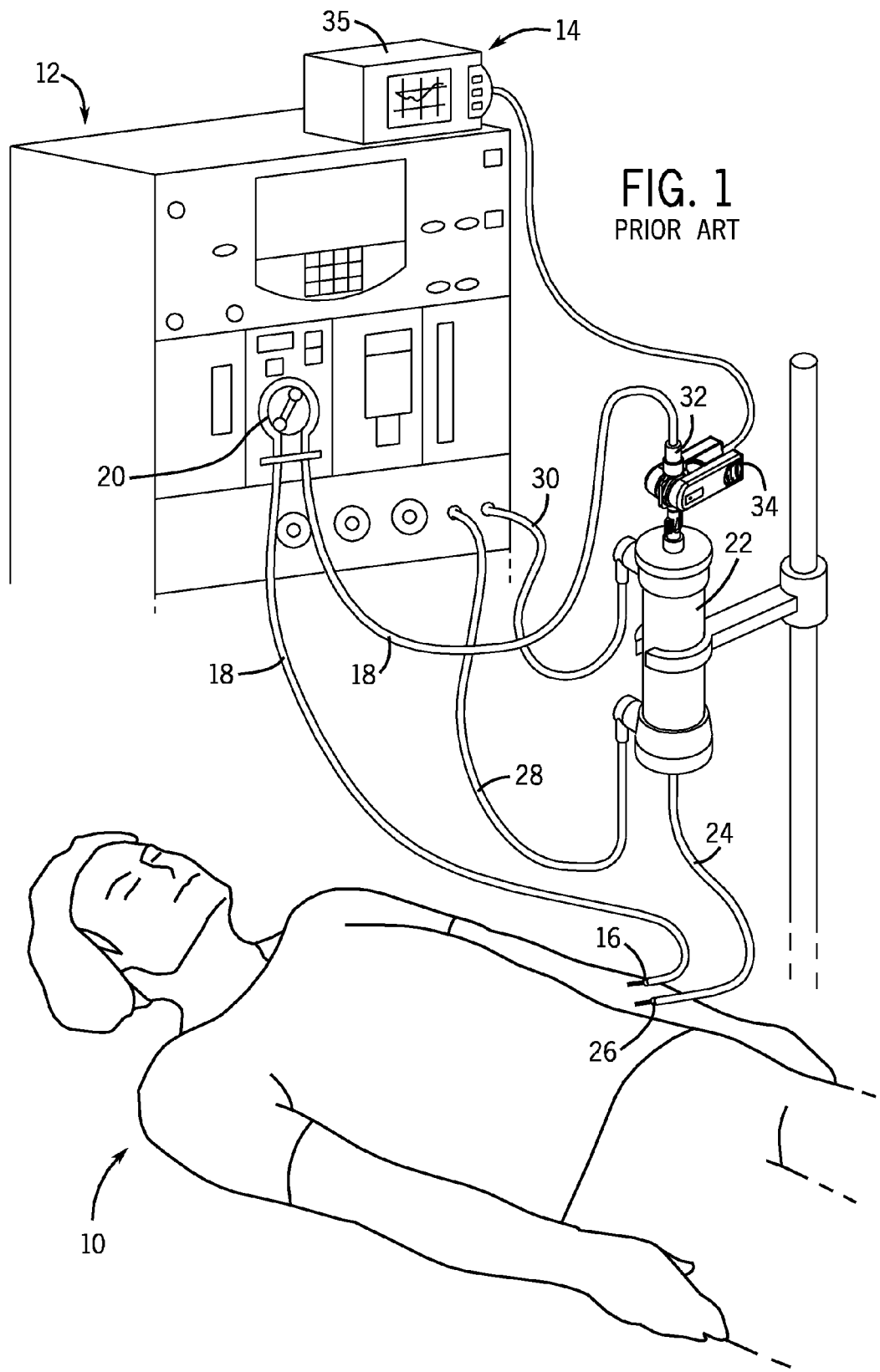
FIG. 1 is a perspective view of a patient undergoing hemodialysis treatment with a non-invasive, optical blood monitor monitoring the patient's blood in real-time as it passes through extracorporeal tubing in the hemodialysis system.

FIG. 1 illustrates a patient 10 undergoing hemodialysis treatment with a conventional hemodialysis system 12, and also illustrates a non-invasive, optical blood monitor 14. A typical hemodialysis clinic will have several hemodialysis systems 12 for treating patients.

An input needle or catheter 16 is inserted into an access site of the patient 10, such as shunt in the arm, and is connected to extracorporeal tubing 18 that leads to a peristaltic pump 20 and then to a dialyzer or blood filter 22. The dialyzer 22 removes toxins and excess fluid from the patient's blood. The dialysized blood is returned from the dialyzer 22 to the patient through extracorporeal tubing 24 and a return needle or catheter 26. The extracorporeal blood flow receives a heparin drip to prevent clotting although that is not shown in FIG. 1. Excess fluids and toxins are removed by clean dialysate liquid which is supplied to the dialyzer 22 via tube 28 and removed for disposal via tube 30. A typical hemodialysis treatment session in the United States takes about 3 to 5 hours. In a typical hemodialysis treatment as described in FIG. 1, the access site draws arterial blood from the patient. If no arterial access is available then a venous catheter may be used to access the patient's blood. As mentioned, other dialysis applications such as low flow applications in an intensive care unit and during surgery using Continuous Renal Replacement Therapy (CRRT) can draw venous blood from the patient. Current art indicates that oxygen saturation levels in venous blood correlate to the cardiac output for the patient. The topical blood monitor 14 shown in FIG. 1 can be used in these other hemodialysis applications as well.

The optical blood monitor 14 includes a blood chamber 32, a sensor clip assembly 34, and a controller 35. The blood chamber 32 is preferably located in line with the extracorporeal tubing 18 upstream of the dialyzer 22. Blood from the peristaltic pump 20 flows through the tubing 18 into the blood chamber 32. The preferred sensor assembly 34 includes LED photoemitters that emit light at substantially 810 nm (e.g. 829 nm), which is isobestic for red blood cells, substantially 1300 nm, which is isobestic for water, and at substantially 660 nm, which is sensitive for oxygenated hemoglobin. The blood chamber 32 includes lenses so that the sensor emitters and detector(s) can view the blood flowing through the blood chamber 32, and determine the patient's real-time hematocrit value and oxygen saturation value using ratiometric techniques generally known in the prior art.

Figure 2:
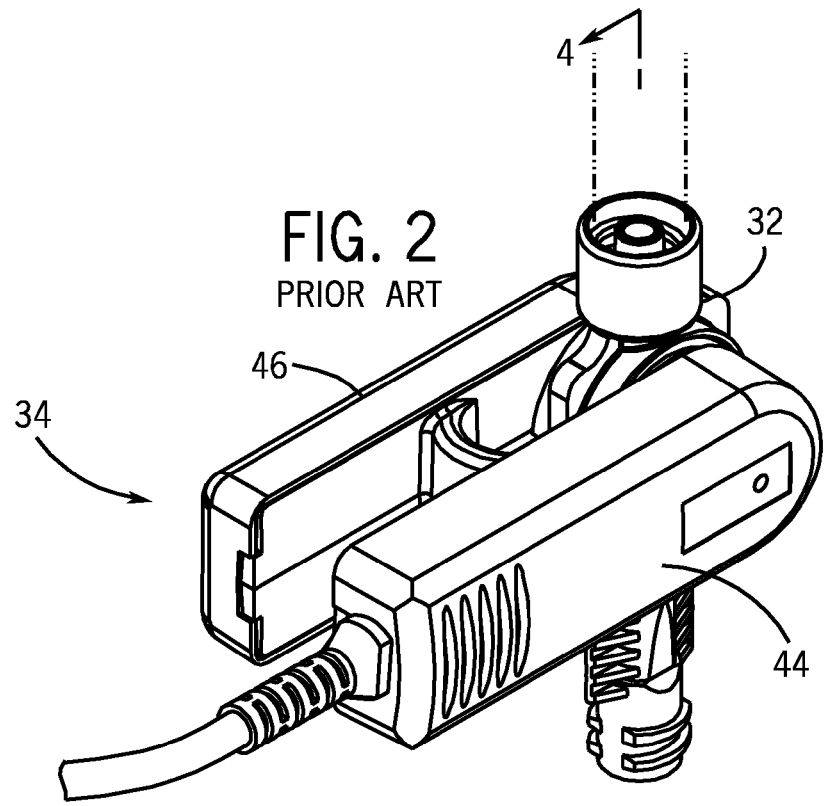
FIG. 2 is a perspective view showing a sensor assembly for the optical blood monitor positioned to sense blood flowing through a prior art blood chamber connected in the extracorporeal tubing of the hemodialysis system.
Figure 3:
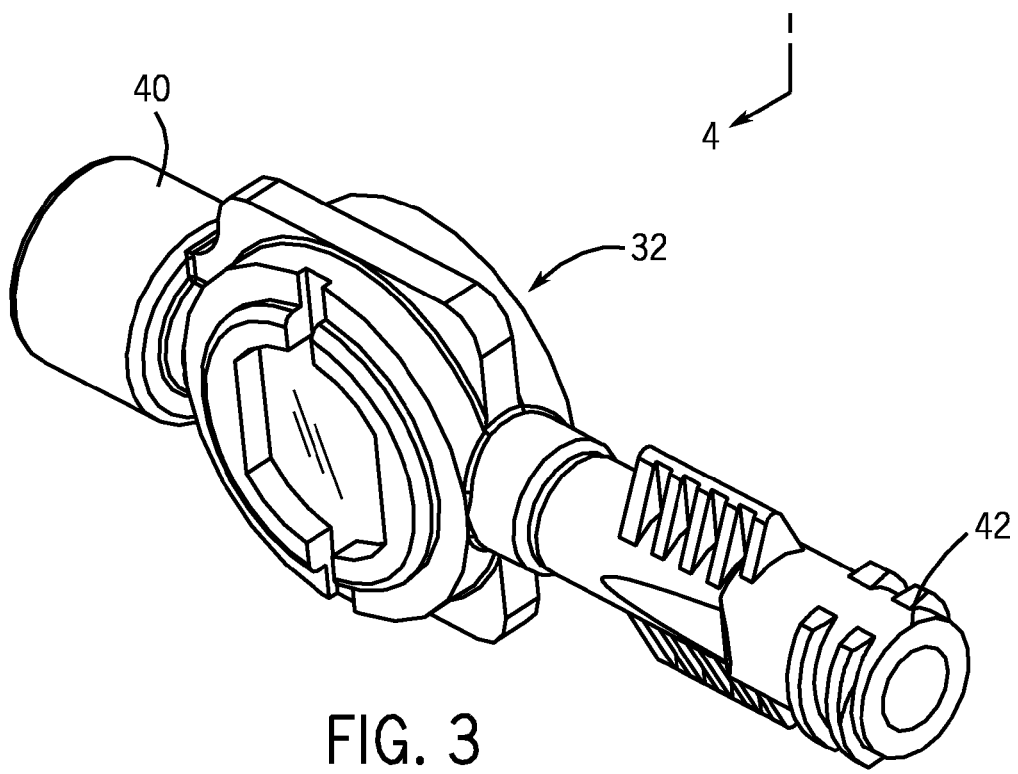
FIG. 3 is a detailed view of the prior art blood chamber shown in FIG. 2.
Figure 4:
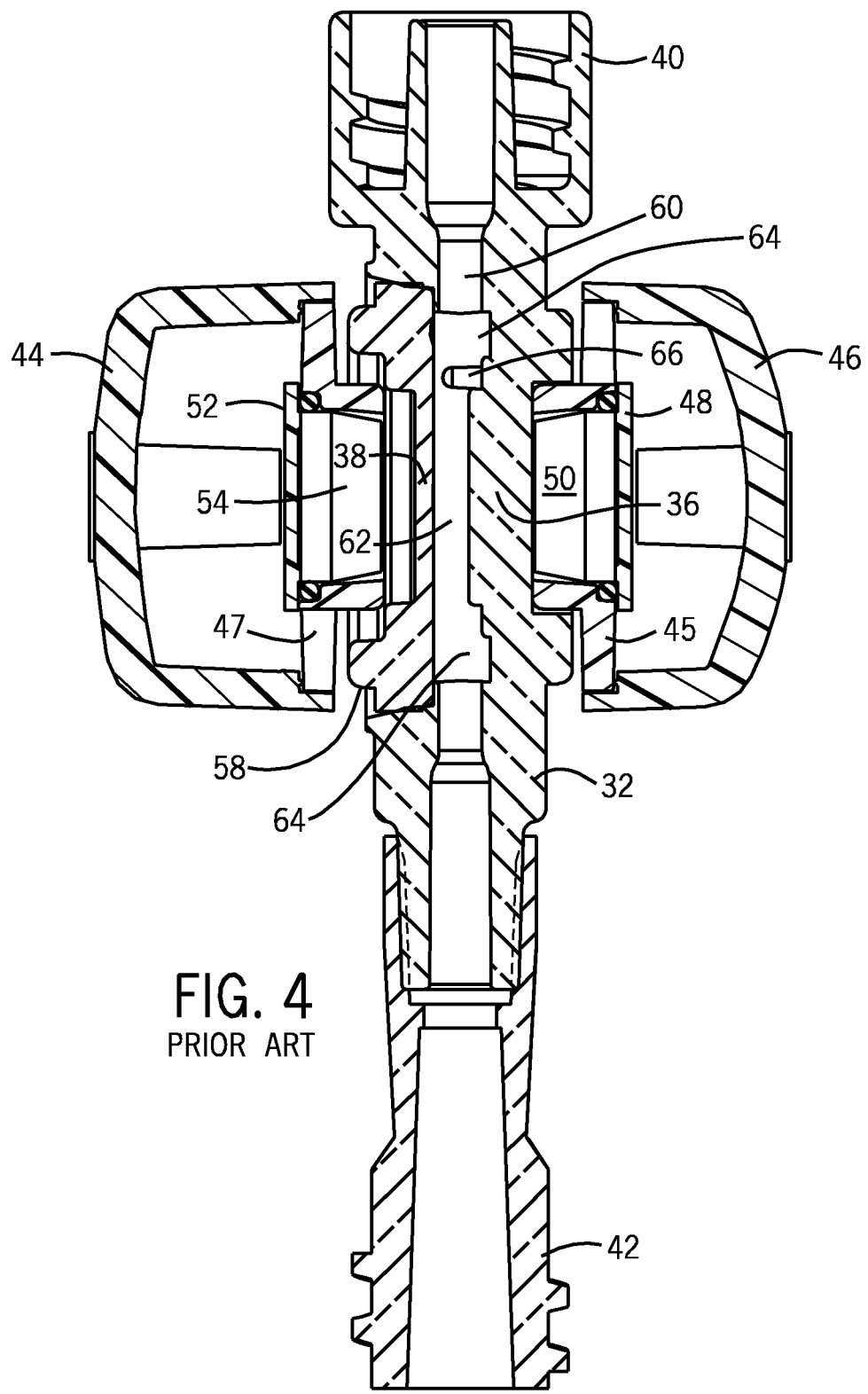
FIG. 4 is a cross-sectional view taken along line 4-4 in FIG. 2.

Referring to now FIGS. 2-4, the body of a prior art blood chamber 32 is made of molded, medical grade, clear polycarbonate. It includes two viewing windows 36, 38 (see FIG. 4). The inlet 40 and outlet 42 are designed to be compatible with standard medical industry connecting devices, conventionally known as luer lock connectors. In the blood chamber 32 shown in FIGS. 2-4, the inlet 40 is integrally molded with the blood chamber 32, whereas the outlet 42 consists of a suitable off-the-shelf connection adapter bonded to the body of the blood chamber 32 or tubing is attached directly to the body in place of connector 42. The sensor clip assembly 34 includes an emitter subassembly 46 and a detector subassembly 44. As best shown in FIG. 4, an LED circuit board 48 containing LEDs emitting visible and infrared light at substantially 660 nm, 810 nm (e.g. 829 nm) and 1300 nm is mounted within the housing for the emitter subassembly 46. The photoemitters on the LED circuit board 48 emits radiation through a molded lens 50 that is mounted in the emitter subassembly 46, and direct the radiation through the viewing window 36 for the blood chamber 32. A detector circuit board 52 contains light photodetectors, at least one made of silicon to detect intensity at 810 nm and 660 nm, and another made of Indium Gallium Arsenide (InGaAs) to detect light intensity at 1300 nm. The controller 35 (FIG. 1) controls the operation of each of the respective LED emitters and detector(s) in order to de-commutate the independent wavelength measurements so only one emitter is active at any given moment in time. The detector circuit board 52 is mounted within the housing for the detector subassembly 44. A molded lens 54 is mounted in the detector subassembly 44.

The viewing window 38 in the blood chamber 32 facilitates transmission of light at the respective wavelengths to the detectors on the photodetector circuit board 52 of the detector subassembly 44. Note that the viewing window 38 is molded into a separate insert 58 (referred to as the lens body 58) that is sonically welded to the body of the blood chamber 32. Blood flows from the inlet 40 through the passageway 60 to a central viewing region 62, also referred to herein as an internal blood flow cavity 62. The internal blood flow cavity provides a substantially flat, thin (e.g. less than 0.1 inches) viewing region for the blood flowing through the blood chamber 32. The pulses of light and infrared radiation at the three selected wavelengths, namely 810 nm, 1300 nm and 660 nm, are transmitted through the blood flowing through the flat viewing region provided by internal blood flow cavity 62, as well as through the viewing windows 36, 38 in the chamber 32. A moat 64 surrounds the flat viewing region 62. The moat 64 is somewhat deeper than the flat viewing region 62. The moat 64 provides a thicker region of blood which under many operating conditions optically isolates the detectors from light or infrared radiation ducted through the chamber body. As mentioned, use of the moat 64 to prevent light ducting is not particularly effective at low hematocrit values (e.g. less than about HCT=15). One or more turbulence posts 66 are located immediately upstream of the viewing region 62 to create steady eddy currents in the flow across the viewing region 62. While the flow through the viewing region 62 is non-laminar, the configuration of the blood chamber 32 shown in FIG. 4 results in steady flow through the viewing region 62 in terms of pressure and flow rate.

The housings 44 and 46 for the sensor clip assembly 34 include an inner housing frame 45, 47 that connects to the respective outer shells 46, 44. The inner housing frames 45, 47 provide an opening into which the molded lenses 50, 54 are mounted. The sensor clip assembly 34 is preferably a spring-loaded clip assembly adapted to be removably mounted to the blood chamber 32, as shown in FIG. 2. Both sides of the blood chamber 32 are molded such that the clip 34 will reside in a predetermined position when mounted to the blood chamber 32. As mentioned, the prior art blood chamber 32 is a single-use clear polycarbonate component. Between patients, the blood chamber 32 is replaced as is the extracorporeal tubing 18 and 24.

Figure 5:
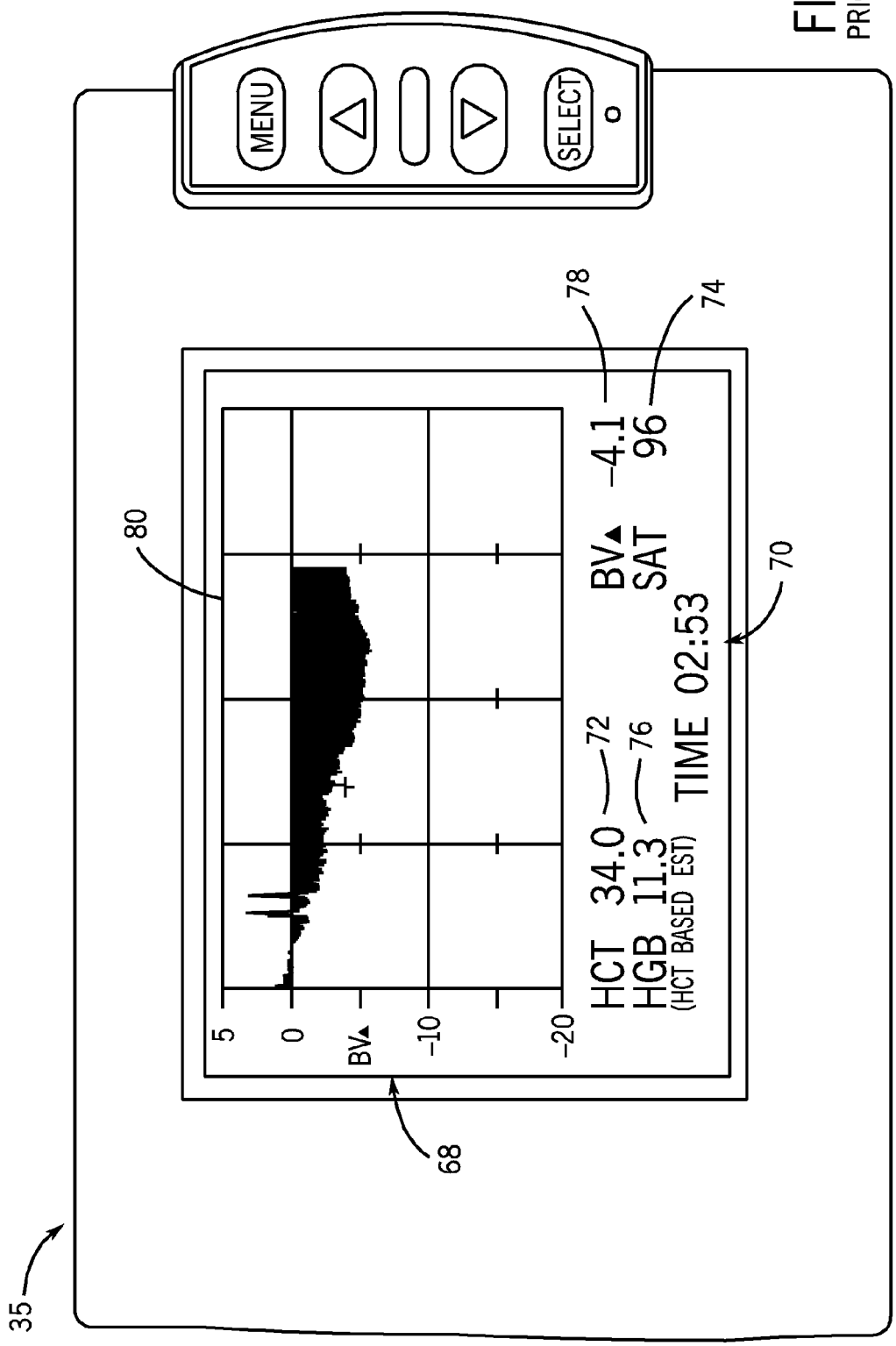
FIG. 5 is a front elevational view of the controller for the optical blood monitor illustrating data including real-time hematocrit (HCT), change in blood volume (BVΔ), hemoglobin (HBG), and oxygen saturation (SAT) levels, as well as the amount of time into the hemodialysis treatment session and a graphical representation of the change in blood volume during the course of the hemodialysis treatment session.

FIG. 5 is a front elevational view of an exemplary controller 35 for the optical blood monitor 14. The controller 35 includes a display 68 that provides real-time blood monitoring data for the patient undergoing hemodialysis. The display 68 in FIG. 5 illustrates the amount of time 70 that the patient 10 has been undergoing hemodialysis for the current treatment session. The time 70 displayed on the screen 68 in FIG. 5 is 2 hours and 53 minutes. The display 68 also illustrates real-time values for the optically monitored hematocrit (HCT) 72 and oxygen saturation (SAT) level 74, as well as the calculated values for hemoglobin (HGB) 76 and change in blood volume (BVΔ), during the treatment session 78. The graph 80 on the display 68 illustrates the change in the patient's blood volume over the course of the 2 hour and 53 minute treatment session. This data is displayed, as shown in FIG. 1, in a location that is located within the vicinity of the patient 10.

Periodically, the calibration and accuracy of the optical blood monitor 14 should be checked. In the art, this is normally done by placing the sensor clip 34 onto a verification filter (made of layered plastic having known optical qualities) that is mounted to the side of the controller 35. Calibration software within the controller 35 verifies the calibration of the unit, or allows the user to field calibrate the unit to bring it back to factory calibration settings. In some instances, it may be necessary to return the unit to the factory for calibration.

Figure 6A:
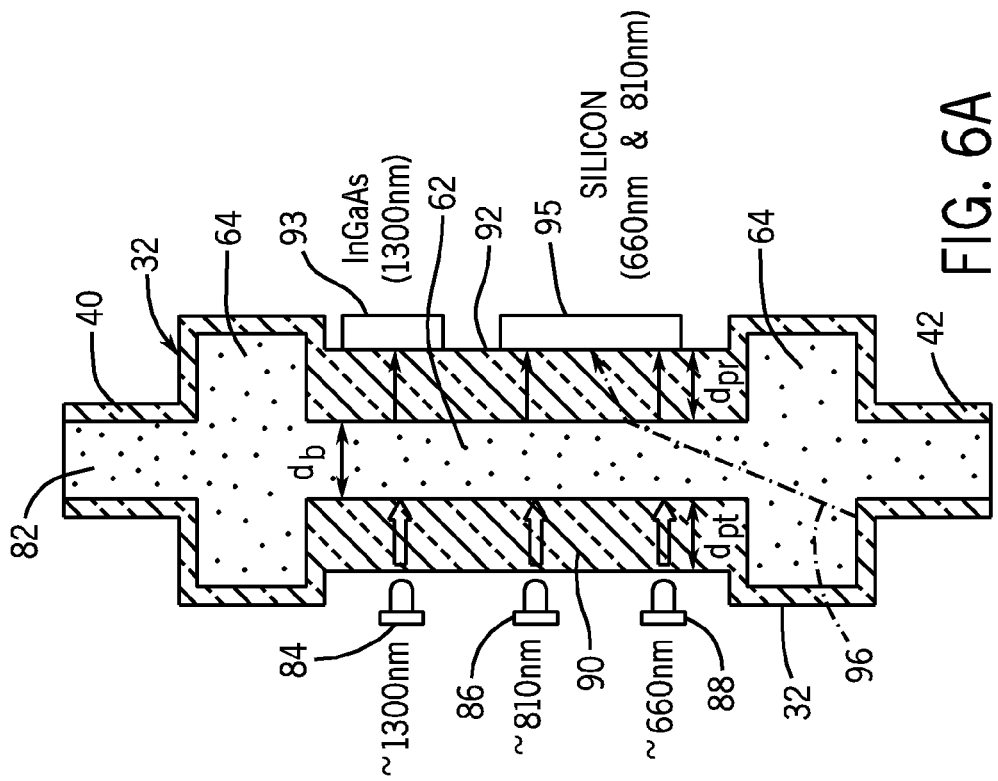
FIG. 6A is a schematic drawing similar to FIG. 6 further illustrating the effect of ducted light.
Figure 6:
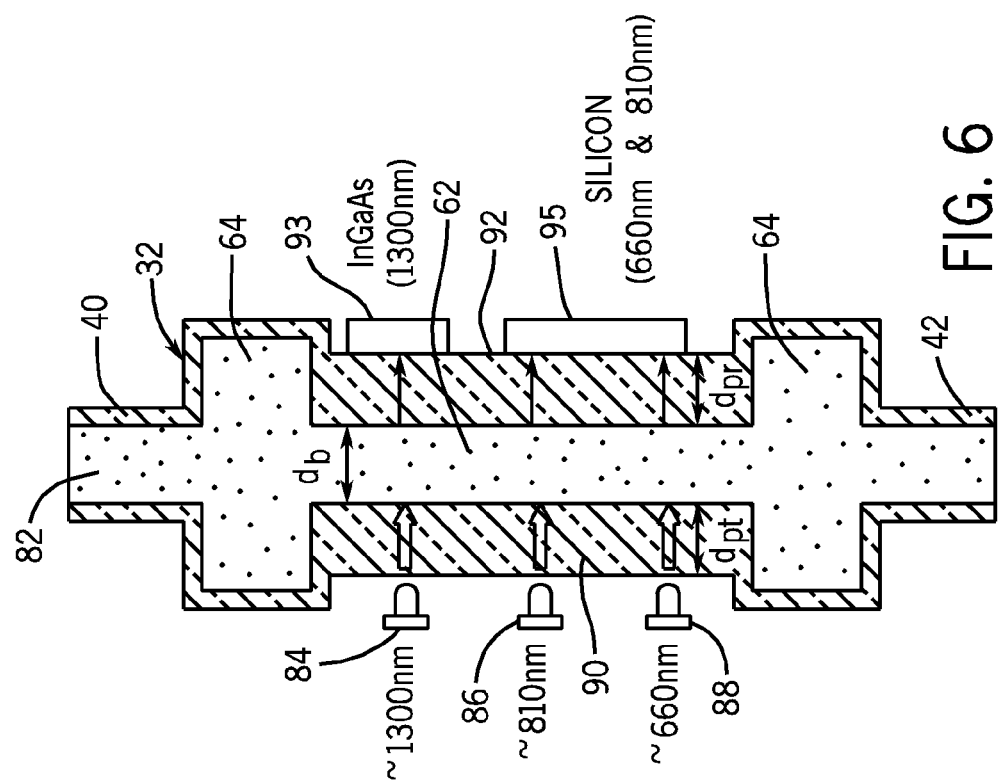
FIG. 6 is a schematic drawing illustrating the detection of light and infrared radiation at various wavelengths through the blood chamber in order to monitor the hematocrit and oxygen saturation of the blood passing through the blood chamber.
Figure 7:
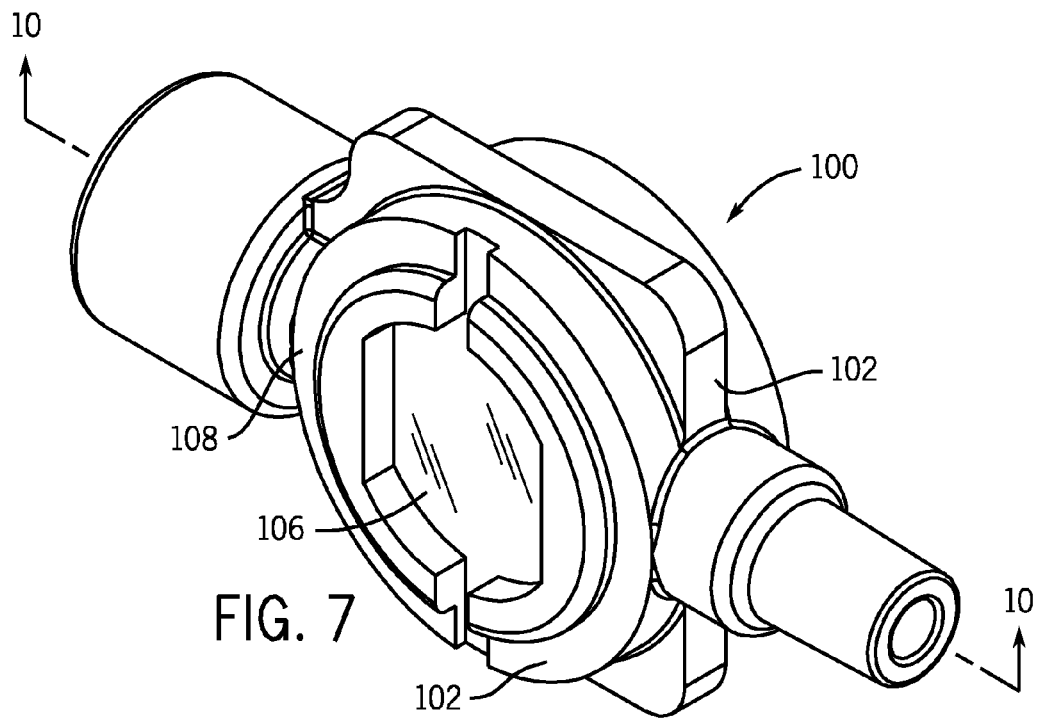
FIG. 7 is a perspective view of a blood chamber constructed in accordance with the first embodiment of the invention.
Figure 8:
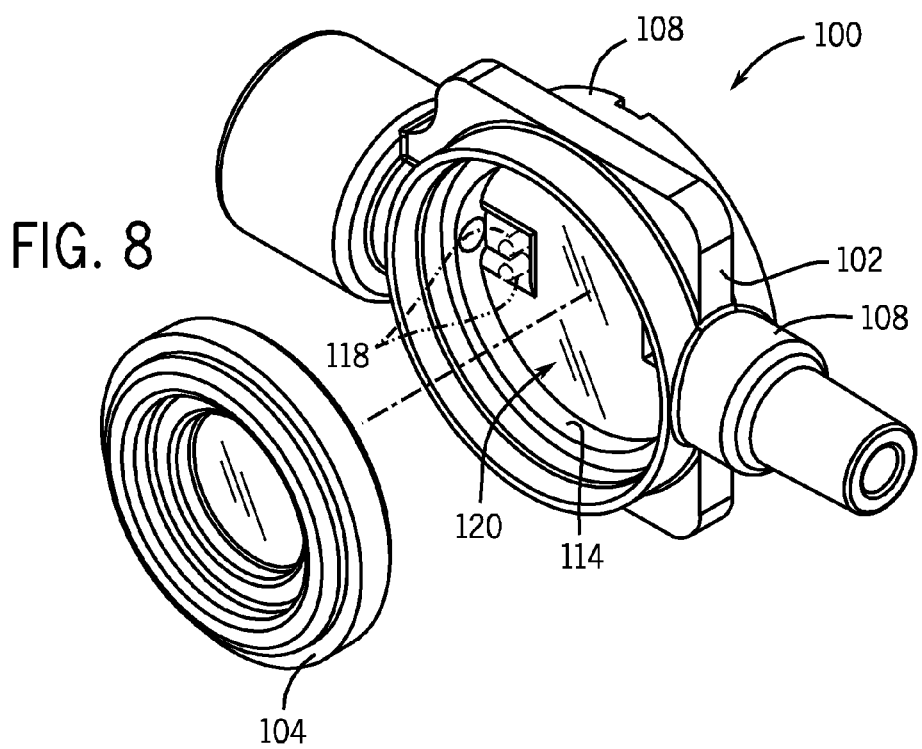
FIG. 8 is a view similar to FIG. 7 showing a lens body exploded away from a chamber body.
Figure 9:
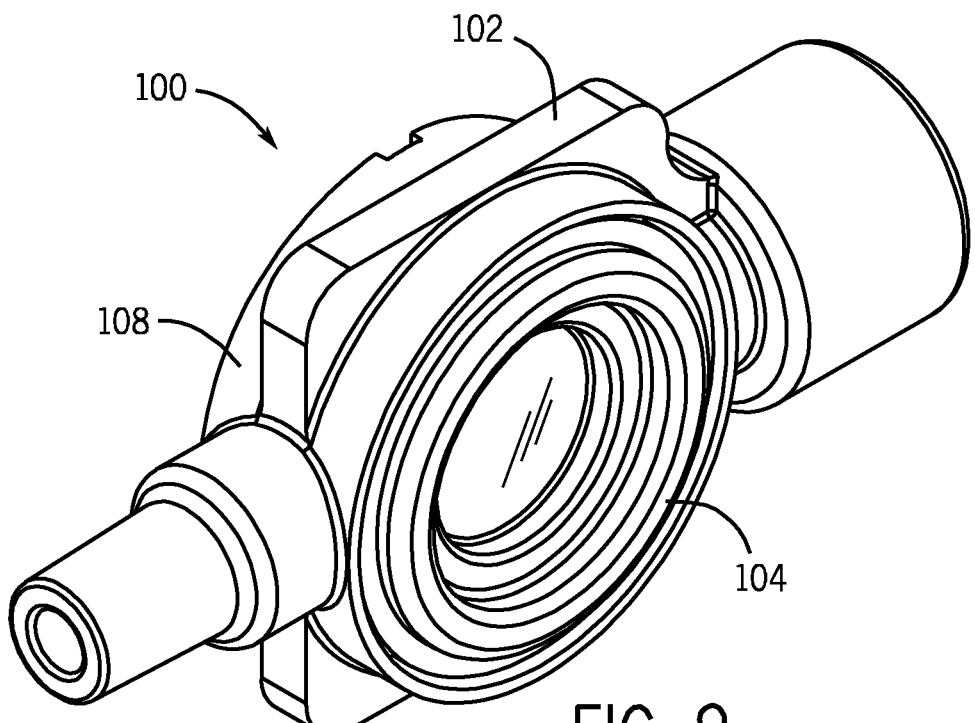
FIG. 9 is a perspective view of back side of the blood chamber shown in FIGS. 7 and 8.

FIG. 6 is a schematic illustration of a prior art blood chamber 32 with a patient's blood 82 flowing through the chamber 32. As described above, the blood 82 enters the blood chamber through an inlet 40 and then flows into a moat 64 surrounding the flat viewing area 62. The distance across the viewing area 62 is given by the arrow labeled $d_b$, which signifies the thickness of the blood flowing through the flat viewing area 62. After the blood leaves the flat viewing area 62, it flows into the moat 64 located on the other side of the viewing area 62 and out of the chamber through the outlet 42. FIG. 6 shows three LED emitters 84, 86 and 88. LED 84 emits infrared light at substantially 1300 nm, LED 86 emits infrared light at substantially 810 nm, and LED 88 emits red light at substantially 660 nm. As mentioned, each of the LEDs 84, 86, 88 emits light at a fixed intensity. The LEDs are pulsed on for a time period such that it is on at a time when the other LEDs are not on (i.e., timed-based multiplexing), although other methods of multiplexing are possible. As shown in FIG. 6, light from each LED emitter 84, 86, 88 is first transmitted through the clear polycarbonate transmission window 90 in the blood chamber 32, then through the blood flowing through the flat viewing region 62, and finally transmitted through the clear polycarbonate receiving window 92 on the other side of the blood chamber 32. An indium gallium arsenide detector 93 detects the intensity of the 1300 nm light wave that is transmitted through the walls of the blood chamber 32 and the blood flowing through the flat viewing region 92. A silicon detector 95 detects the intensity of the light at 810 nm and at 660 nm transmitted through the walls of the blood chamber 32 and the blood flowing through the flat viewing region 92.

The intensity of the light at each of the various wavelengths is reduced by attenuation and scattering from the fixed intensity of the light emitted from each of the LEDs 84, 86, 88. Beers Law, for each wavelength of light, describes attenuation and scattering as follows:

$$i_n = I_{o-n} e^{-\epsilon_p X_p d_{pt}} e^{-\epsilon_b X_b d_b} e^{-\epsilon_p X_p d_{pr}} \quad \text{Eq. (3)}$$

where $i_n$=received light intensity at wavelength n after attenuation and scattering; $I_{on}$=transmitted light intensity at wavelength n incident to the measured medium; e=the natural log exponential term; $\epsilon$=the extinction coefficient for the measured medium (p—polycarbonate, b—blood); X=the molar concentration of the measured medium (p—polycarbonate, b—blood); and d=the distance through the measured medium (pt—transmitting polycarbonate, b—blood, pr—receiving polycarbonate).

Since the properties of the polycarbonate blood chamber do not change, the first and third exponential terms in the above Equation (3) are normally assumed in the prior art to be constants for each wavelength. Mathematically, these constant terms are multiplicative with the initial constant term $I_{on}$ which represents the fixed intensity of the radiation transmitted from the respective LED emitter 84, 86, 88. For simplification purposes, Equation (3) if often rewritten in the following form using bulk extinction coefficients and a modified initial constant $I'_{on}$ as follows:

$$i_n = I'_{o-n} * e^{-\alpha_b d_b} \quad \text{Eq. (4)}$$

where $i_n$=received light intensity at wavelength "n" after attenuation and scattering as though the detector were at the receive blood boundary; $\alpha$=the bulk extinction coefficient for blood; $\alpha_b = \epsilon_b X_b$; and $I'_{o-n}$=the equivalent transmitted radiation intensity at wavelength n boundary accounting for losses through the blood chamber walls.

Using the approach defined in Equation (4) above, the 810 nm wavelength which is isobestic for red blood cells and the 1300 nm wavelength which is isobestic for water can be used to determine the patient's hematocrit. The ratio of the normalized amplitudes of the measured intensity at these two wavelengths produces the ratio of the composite extinction values α for the red blood cells and the water constituents in the blood chamber, respectively. Therefore, the following mathematical function defines the measured HCT value:

$$HCT = f\left[\frac{\ln\left(\frac{i_{810}}{I_{0-810}}\right)}{\ln\left(\frac{i_{1300}}{I_{0-1300}}\right)}\right] \quad \text{Eq. (5)}$$

where $i_{810}$ is the detected infrared intensity of the photoreceiver 95 (FIG. 6) at 810 nm, $i_{1300}$ is the detected infrared intensity of the photodetector 93 (FIG. 6) at 1300 nm and $I_{0810}$ and $I_{01300}$ are constants representing the infrared radiation intensity incident on the blood accounting for losses through the blood chamber at 810 nm and 1300 nm respectively. The above equation holds true assuming that the flow of blood through the blood chamber 32 is in steady state, i.e. steady pressure and steady flow rate. This assumption is accurate in part because the moat 64 helps to maintain the blood in steady state.

The preferred function f[ ] is a second order polynomial having the following form:

$$HCT = f = A\left[\frac{\ln\left(\frac{i_{810}}{I_{0-810}}\right)}{\ln\left(\frac{i_{1300}}{I_{0-1300}}\right)}\right]^2 + B\left[\frac{\ln\left(\frac{i_{810}}{I_{0-810}}\right)}{\ln\left(\frac{i_{1300}}{I_{0-1300}}\right)}\right] + C. \quad \text{Eq. (6)}$$

A second order polynomial is normally adequate as long as the infrared radiation incident at the first and second wavelengths is substantially isobestic.

The oxygen saturation level, or the oxygenated hemoglobin level, is determined using a ratiometric equation for the intensity of red light at 660 nm detected by detector 95, FIG. 6 and the intensity of infrared light at 810 nm detected by detector 95, FIG. 6. The form of the ratiometric model for determining oxygen saturation level is as follows:

$$SAT = g\left[\frac{\ln\left(\frac{i_{660}}{I_{0-660}}\right)}{\ln\left(\frac{i_{810}}{I_{0-810}}\right)}\right] \quad \text{Eq. (7)}$$

where $i_{660}$ is the detected intensity of the photoreceiver at 660 nm, $i_{829}$ is the detected intensity of the photodetector at 810 nm and $I_{0660}$ and $I_{0829}$ are constants representing the intensity incident on the blood accounting for losses through the blood chamber. The function g[ ] is a mathematical function based on experimental data to yield the oxygen saturation level, again preferably a second order polynomial $$SAT = g = A\left[\frac{\ln\left(\frac{i_{660}}{I_{0-660}}\right)}{\ln\left(\frac{i_{810}}{I_{0-810}}\right)}\right]^2 + B\left[\frac{\ln\left(\frac{i_{660}}{I_{0-660}}\right)}{\ln\left(\frac{i_{810}}{I_{0-810}}\right)}\right] + C. \quad \text{Eq. (8)}$$

Errors in the oxygen saturation value (SAT) can occur if there are errors in the measured light intensity at either the 660 nm or 810 nm wavelength. As mentioned, it has been found that the most prolific source of such errors is ducted red light (660 nm) through the blood chamber. As mentioned previously, the dynamic range of the expected 660 nm signal is about 500:1. At low hematocrit values (e.g. less than about 15 HCT) the current blood chamber is not particularly effective at attenuating ducted light. Due to the resolution needed at very low oxygen saturation levels, error caused by ducted light can compromise oxygen saturation readings at low hematocrit levels.

Present Invention

FIG. 6A is a schematic drawing illustrating a signal ray 96 of ducted light radiation, and in particular a single ray of red light having a wavelength of about 660 nm that is sensed by the photodetector 95. Light piping occurs when the incident angle of the light from the LED (e.g. 660 nm light wave from the LED 88) at the boundary of the chamber 32 and the blood 82 is smaller than the critical angle defined by Snell's Law. In this circumstance, the light reflects into the blood chamber material 32 rather than passing through the blood 82 directly to the photodetector 95. Due to the geometry of the blood chamber 32 and the ability of the clear polycarbonate material in the prior art blood chamber 32 to transmit light via reflection/refraction, ducted light can take many unique paths prior to being refracted towards the detector 95. In actuality, the resulting signal at the photodetector 95 is the summation of all direct and all piped rays that arrive at that location. Because the wavelength of the light is comparatively small, virtually any change in the manufacturing tolerance from blood chamber to blood chamber will negate any ability to fully and predictably characterize a transfer function for the piped or ducted light. Ducting is a function (but not limited to) the material of the blood chamber 32, the blood chamber dimensions, the number of reflections/refractions from the LED emitter to the photodetector, the wavelength of the light or infrared radiation, and the total path of distance traveled. For simplicity and analysis, the intensity of piped light at the detector ($i_p$) is a function of several variables:

$$i_p = p(v_1, v_2, v_3 \ldots v_n)Io \quad \text{Eq. (9)}$$

where:
$I_o$=the impressed intensity from the LED photoemitter at the wavelength of interest;
$i_p$=the received intensity from the direct piping path at the photodetector;
p=the piping function of several variables—$v_1, v_2, v_3, \ldots v_n$ The total intensity received at the photodetector 95 will be the resultant sum of the individual light signals arriving at the photodetector 95. Because light exhibits both particle and wave characteristics, it is reasonable to conclude that this summation will be in vector form comprised of the vector sums of the amplitude at the respective phases of each respective light component. In general:

$$i = i_s + i_p \quad \text{Eq. (10)}$$

where:
i=the total intensity signal summed and integrated into a current at the photodetector
$i_s$=the component of light arriving from the LED 88 along the signal path $d_b$
$i_p$=the component of light arriving from the LED 88 through light piping paths.

With ducting present, Equation (8) must be modified by $i_p$ added to each ratiometric term $i_s$. Since $i_p$ and the ratiometric term $i_s$ do not change proportionally, the polynomial, g, has no solution and cannot be determined if the value of $i_p$ is significant compared to the ratiometric term $i_s$.

Considering that the total intensity signal (i) includes both the component ($i_s$) for the direct signal path ($d_b$) and the components of ducted light ($i_n$), it becomes difficult if not impossible to determine an adequately reliable function g[ ] for the above Equation (7) over the full dynamic range necessary to measure oxygen saturation levels, when the patient's hematocrit is low so that the light piping signals 96 are not attenuated by blood in moat 64 of the blood chamber. Efforts to mathematically account for light piping errors have to date been difficult to achieve. In accordance with the invention, it has been found that the preferred method is to eliminate the intensity of piped light detected by the photodetector 95. This is done in accordance with the invention by adding materials or tinting to the blood chamber body that absorbs the light at the appropriate wavelengths as it travels through the blood chamber body, thereby eliminating light piping terms from the necessary mathematics for the ratiometric model.

Figure 10:
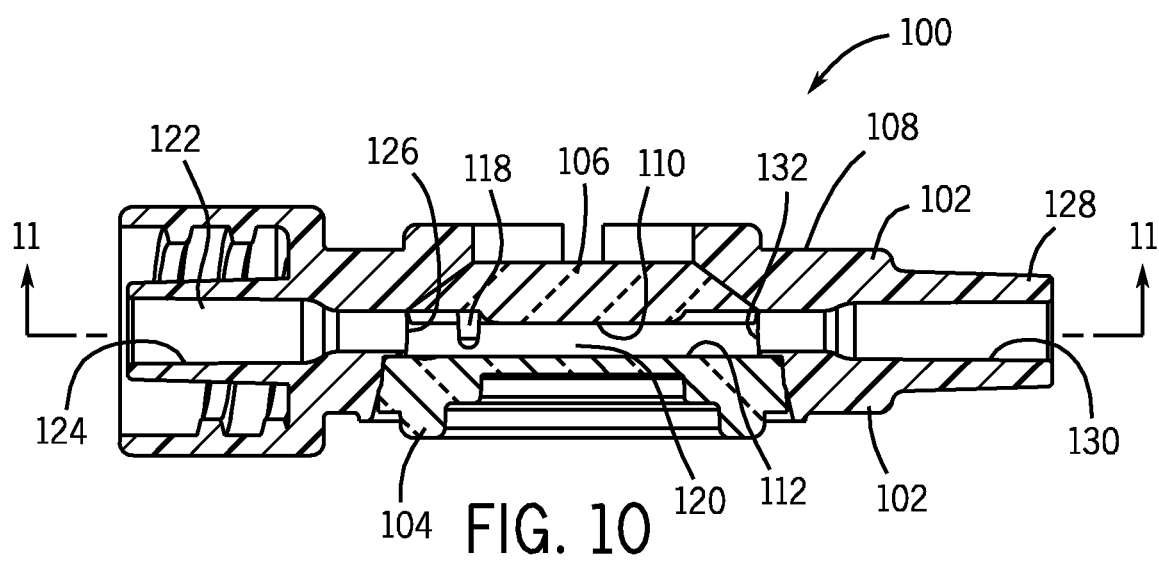
FIG. 10 is a longitudinal sectional view taken along line 10-10 in FIG. 7.
Figure 11:
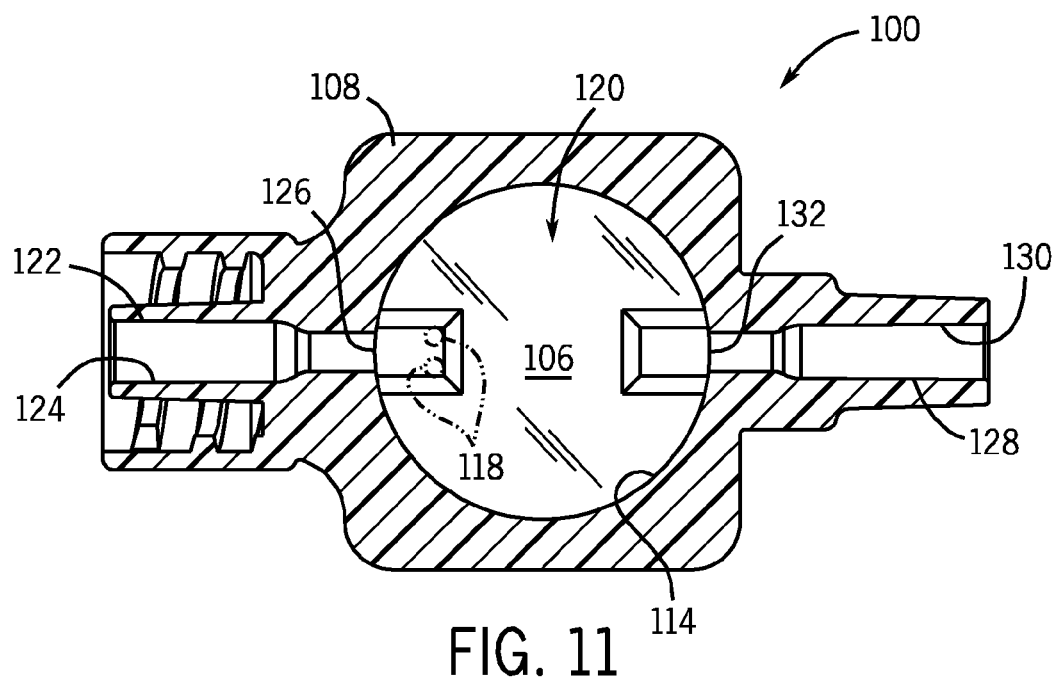
FIG. 11 is a sectional view taken along line 11-11 in FIG. 10.

FIGS. 7 through 11 illustrate a blood chamber 100 in accordance with the first embodiment of the invention. The blood chamber 100 is similar in many respects to the prior art blood chamber 32 shown in FIGS. 3 and 4; however, the blood chamber 100 has a chamber body 102 that includes a blue-tinted portion 108 in order to attenuate light ducting at the 660 nm wavelength. Referring in particular to FIG. 10, the lens 106 on the chamber body 102 is preferably made of clear, medical grade polycarbonate material which is molded with a polished finish in order to facilitate reliable light transmission, e.g. Bayer Makrolon FCR2458-55115 (no regrind allow), which is blood contact approved, USP XX11, Class V1. It is expected that the material be certified as to grade number, lot number and date of manufacture. No mold release should be used, and any lubrications should be food grade and not silicon based. The molded parts should be produced with no loose foreign material greater than 0.1 mm² and no embedded foreign material greater than 0.2 mm². The mold finish is preferably SPIA3 (scale) except along the surfaces for the viewing windows in which the finish is preferably at least SPIA1. Moreover, the viewing windows should contain no splay, bubbles or marks when looking through the display window viewed from 12" with the normal eye. Parts should be cleaned and free of dirt, oils and other foreign matters before use. The clear lens portion 106 is preferably molded prior to overmolding the remaining blue-tinted portion of the chamber body 102. More specifically, the clear lens portion 106 is placed in the mold, while the blue-tinted portion 108 of the chamber body is over molded. The material of the blue-tinted portion 108 should be compatible with the material of the clear lens portion 106, and preferably is the same material (medical grade polycarbonate) except for the tinting. Compatibility of the materials is important because it is unacceptable for leaking to occur at the seam between the clear lens portion 106 and the remaining blue-tinted portion 108.

The blue-tinted portion 108 is preferably tinted in a dark blue which is opaque and not transparent to red light in general, and in particular red light having a wavelength of about 660 nm. A suitable blue-tint for the polycarbonate material for this purpose is Pantone PMS 2935. Lighter tints such as Pantone PMS 2707 are less suitable.

It should be noted that the blood chamber 100 in FIGS. 8-11 does not include a moat surrounding the viewing area within the blood flow cavity 120. As mentioned, it may be desirable to remove the moat from the blood chamber if the system is able to eliminate the effects of ambient light, for example through the use of appropriate signal processing.

The lens body 104 is preferably made entirely of clear, medical-grade polycarbonate, and is sonically welded into place on the chamber body 102. The overmolded lens 106 in the chamber body 102 includes a substantially flat internal wall 110 which forms part of the internal blood flow cavity 120. The lens body 104 includes a substantially flat internal wall 112.

The chamber body includes a substantially flat internal wall 110 which forms part of the internal blood flow cavity 120. When the lens body 104 is attached to the chamber body 102, the flat internal wall 112 on the lens body 104 is substantially parallel to the flat internal wall 110 on the chamber body 102. The flat internal wall 112 on the lens body 104 is separated from the flat internal wall 110 on the chamber body 102 by a predetermined fixed distance. The clear portions 106 on the overmolded chamber body 102 and the lens body 104 commensurate with at least a portion of the flat internal walls 110, 112 serve as viewing windows for blood flowing through the internal blood flow cavity 120. The blood flow cavity 120 is defined by the flat internal walls 110, 112 as well as a peripheral wall 114 (FIG. 8) on the chamber body 102 that extends between the periphery of the flat internal walls 110, 112 when the lens body 104 is welded into place. The chamber body 102 includes a first port 122 and a channel 124 which are in fluid communication through a first opening 126 in the peripheral wall 114 with the internal blood flow cavity 120.

The chamber body 102 also includes a second port 128 and channel 130 which are in fluid communication through a second opening 132 in the peripheral wall 114 with the internal blood flow cavity 120. In the embodiment shown on FIGS. 7 through 11, the second port 128 and channel 130 are in axial alignment with the first port 122 and channel 124 along an axis that spans across the middle of the internal blood flow cavity 120. The chamber body 102 also includes turbulence post 118 which ensures robust, non-laminar flow through the viewing area in the internal blood flow cavity 120. As mentioned, the internal flow cavity 120 in the embodiment shown in FIGS. 7-11 does not include a moat around the periphery of the viewing area.

Figure 12:
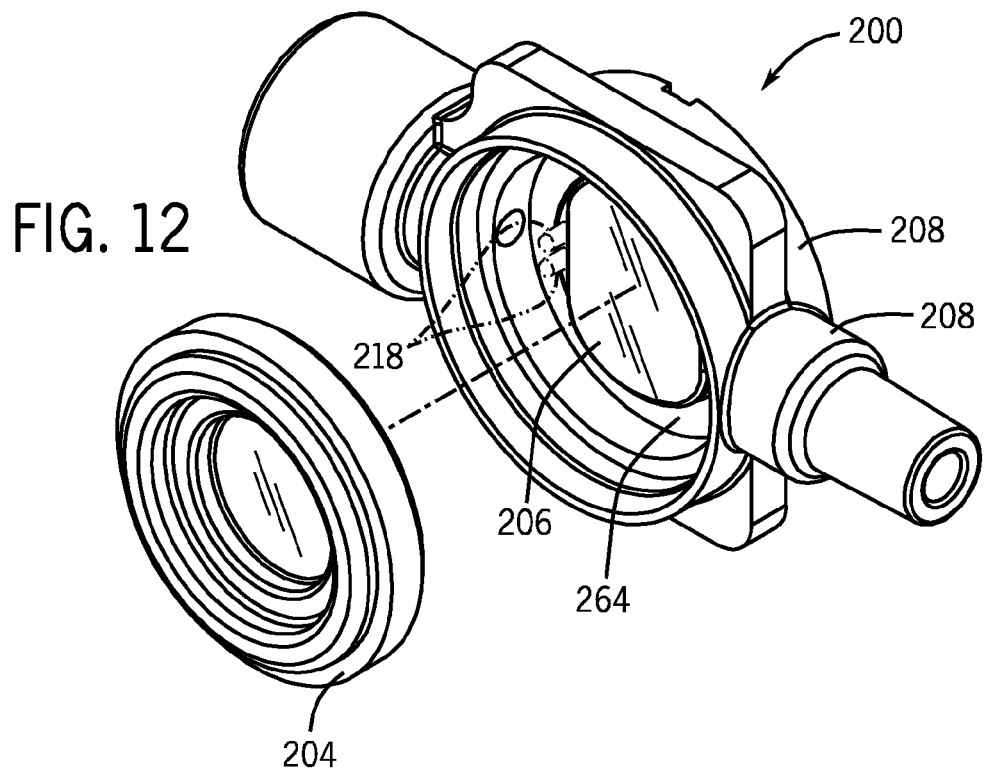
FIG. 12 is a view similar to FIG. 8 illustrating a second embodiment of the invention.

FIGS. 12 through 14 illustrate a blood chamber 200 constructed in accordance with a second embodiment of the invention. Blood chamber 200 includes a moat 264 surrounding the internal blood flow cavity 220 as in the prior art blood flow chamber 32 illustrated in FIGS. 3 and 4. In fact, the structure and dimensions of the blood chamber 200 shown in FIGS. 12 through 14 are substantially the same as those shown in the prior art blood chamber 32, with the primary difference being that portion 208 of the blood chamber body 202 in FIGS. 12 through 14 is made of a blue-tinted material, such as dark blue tinted polycarbonate, in order to alternate ducted red light particularly at 660 nm if the LED emitter 88 emits red light at 660 nm. Because of the presence of the moat 264, ducting of the infrared radiation through the chamber body 202 (or ambient light) is even less likely to cause errors in the mathematics pertaining the ratiometric models for determining the real-time oxygen saturation and hematocrit levels.

As with the blood chamber 100 shown in FIGS. 7 through 11, the viewing lens 206 on the chamber body 202 is preferably made of clear, polished polycarbonate material, and the remaining portion 208 of the chamber body 202 is over molded to the lens portion 206. As mentioned previously, the opaque (blue-tinted) portion 208 of the chamber body 202 is preferably made of the same material as the clear lens portion 206, but tinted blue in order to block the transmission of red light occurring at the relevant wavelengths, e.g. about 660 nm. As in the previous embodiments, the lens body 204 is made of clear material, e.g. clear polycarbonate, that is sonically welded to the chamber body 202.

The described use and embodiment of the invention is to be considered in all respects as only illustrative and not restrictive.

What is claimed is:

1. A blood chamber connected to an extracorporeal tube for optically monitoring blood flowing through the extracorporeal tube, the chamber comprising:
    a chamber body forming an internal blood flow cavity which provides flow path for the flowing blood and includes a flat viewing area for optical monitoring of the blood using a photoemitter and a photodetector;
    a portion of the chamber body outside the flat viewing area tinted blue and opaque to red light and otherwise transparent to visible light, wherein the blue-tinted portion of the chamber body is configured to attenuate red light out of ambient light that enters the internal blood flow cavity through the chamber body;
    opposing lenses of clear material disposed in the flat viewing area of the chamber body for transmitting light from the photoemitter through the internal blood flow cavity; and
    a peripheral wall extending around each of the opposing lenses for mating with a clip that includes the photoemitter and the photodetector.

2. The blood chamber as recited in claim 1 wherein the opposing lenses are molded from clear polycarbonate material and the blue-tinted portion of the chamber body is molded from a blue-tinted polycarbonate material.

3. The blood chamber as recited in claim 1 wherein the blue tinted portion of the chamber body is welded to a first lens of the opposing lenses.

4. The blood chamber as recited in claim 1 wherein the blue tinted portion of the chamber body is made of a material that is opaque to a full spectrum of red light.

5. The blood chamber as recited in claim 1 wherein an entirety of each of the opposing lenses is molded from clear polycarbonate material.

6. The blood chamber as recited in claim 1 wherein the internal flow cavity includes a moat around a viewing area between the opposing lenses.

7. The blood chamber as recited in claim 1 wherein the chamber body includes input and output ports axially aligned along an axis across the blood chamber.

8. An optical blood monitoring system comprising:
extracorporeal tubing for passing blood drawn from a patient;
a blood chamber receiving blood flowing through the extracorporeal tubing, the blood chamber defining a flow path through an internal blood flow cavity and providing an area for optical monitoring of the blood, the blood chamber including
a chamber body comprising a flat internal wall and a peripheral wall extending around the flat internal wall, the flat internal wall and the peripheral wall forming part of the internal blood flow cavity,
a viewing lens made of a clear material commensurate with at least a portion of the flat internal wall of the chamber body to provide optical access to blood flowing through the internal blood flow cavity, and
at least a portion of the chamber body tinted blue, wherein the blue-tinted portion of the chamber body is configured to be opaque to red light at a third wavelength ($\lambda_3$) and otherwise transparent to visible light, and to attenuate red light at the third wavelength ($\lambda_3$) out of ambient light that enters the internal blood flow cavity through the chamber body;
a lens body having a flat internal wall that is attached to or formed integrally with the chamber body to form the internal blood flow cavity along with the flat internal wall and peripheral wall of the chamber body, wherein the lens body is attached to the chamber body with the flat internal wall of the lens body being substantially parallel to the flat internal wall of the chamber body and also being separated from the flat internal wall of the chamber body by a predetermined fixed distance, and the lens body comprises a viewing lens made of a clear material commensurate with at least a portion of the flat internal wall on the lens body to provide optical access to blood flowing through the internal blood flow cavity; and
a sensor assembly that monitors the patient's blood flowing through the blood chamber, the sensor assembly comprising a third photoemitter for emitting red light at the third wavelength ($\lambda_3$) through the viewing lenses and blood flowing through the internal blood flow cavity of the blood chamber, a first photoemitter for emitting infrared light at a first wavelength ($\lambda_1$) through the viewing lenses and the blood flowing through the internal blood flow cavity of the blood chamber, and at least one photodetector for detecting the intensity of the light at each of the third ($\lambda_3$) and first ($\lambda_1$) wavelengths after the light passes through the viewing lenses and blood flowing through the internal blood flow cavity of the blood chamber.

9. The optical blood monitoring system as recited in claim 8 wherein the viewing lenses are molded from clear polycarbonate material and the portion of the chamber body tinted blue is molded from a tinted blue polycarbonate material.

10. The optical blood monitoring system as recited in claim 8 wherein the viewing lenses are molded from clear polycarbonate material and the portion of the chamber body tinted blue is molded from a blue-tinted polycarbonate material.

11. The optical blood monitoring system as recited in claim 8 wherein the blue tinted portion of the chamber body is made of a material that is opaque to a full spectrum of red light.

12. The optical blood monitoring system as recited in claim 8 wherein an entirety of each of the viewing lenses is molded from clear polycarbonate material.

13. The optical blood monitoring system as recited in claim 8 wherein the internal flow cavity includes a moat around a viewing area between the viewing lenses.

14. The optical blood monitoring system as recited in claim 8 wherein the chamber body includes axially aligned input and output ports.

15. A blood chamber connected to an extracorporeal tube for optically monitoring blood flowing through the extracorporeal tube, the chamber comprising:
a chamber body forming an internal blood flow cavity which provides a flow path for the flowing blood and includes a flat viewing area for optical monitoring of the blood, the chamber body including means for attenuating red light out of ambient light that enters the internal blood flow cavity through the chamber body while maintaining the chamber body transparent so as to allow visualization of blood flowing through the internal blood flow cavity;
opposing lenses of clear material disposed in the flat viewing area of the chamber body for transmitting light from a photoemitter through the internal blood flow cavity; and
a peripheral wall extending around each of the opposing lenses for mating with a clip that includes the photoemitter.

16. The blood chamber as recited in claim 15 wherein the opposing lenses are molded from clear polycarbonate material and the means for attenuating red light includes a portion of the chamber body molded from a blue-tinted polycarbonate material.

17. The blood chamber as recited in claim 15 wherein the chamber body includes axially aligned input and output ports.

* * * * *